(12) United States Patent
McGrath

(10) Patent No.: US 9,414,743 B2
(45) Date of Patent: Aug. 16, 2016

(54) LARYNGOSCOPE

(75) Inventor: Matthew John Ross McGrath, Edinburgh (GB)

(73) Assignee: AIRCRAFT MEDICAL LIMITED, Edinburgh (GB)

( * ) Notice: Subject to any disclaimer, the term of this patent is extended or adjusted under 35 U.S.C. 154(b) by 531 days.

(21) Appl. No.: 12/675,892

(22) PCT Filed: Aug. 28, 2008

(86) PCT No.: PCT/GB2008/002903
§ 371 (c)(1),
(2), (4) Date: Jun. 7, 2010

(87) PCT Pub. No.: WO2009/027672
PCT Pub. Date: Mar. 5, 2009

(65) Prior Publication Data
US 2010/0312059 A1 Dec. 9, 2010

(30) Foreign Application Priority Data
Aug. 28, 2007 (GB) .................................. 0716672.1

(51) Int. Cl.
*A61B 1/267* (2006.01)
*A61M 16/04* (2006.01)

(52) U.S. Cl.
CPC ............ *A61B 1/267* (2013.01); *A61M 16/0488* (2013.01)

(58) Field of Classification Search
CPC ..... A61B 1/267; A61B 1/2673; A61B 1/2676
USPC .............. 600/120, 184–200, 237; 128/200.26
See application file for complete search history.

(56) References Cited

U.S. PATENT DOCUMENTS 2,648,329 A * 8/1953 Morch .......................... 600/193
3,153,267 A * 10/1964 Rowland, Jr. ................. 600/241
(Continued)

FOREIGN PATENT DOCUMENTS

EP 0 284 335 9/1988
EP 1 598 001 11/2005
(Continued)

OTHER PUBLICATIONS

International Search Report for PCT/GB2008/002903, mailed Dec. 12, 2008.
(Continued)

*Primary Examiner* — Christian Sevilla
*Assistant Examiner* — Eric S Gibson
(74) *Attorney, Agent, or Firm* — Fletcher Yoder PC

(57) ABSTRACT

Disclosed is a laryngoscope comprising a handle and an insertion section which extends from the handle, wherein the insertion section comprises a tube guide for retaining and guiding an endotracheal tube during intubation, wherein the handle comprises at least one external tube engaging formation, such as a tube guiding member or tube retaining member. There is also disclosed a laryngoscope having a handle and insertion section which adapted to detachably retain and guide an endotracheal tube along a lateral side of the insertion section and handle such that a retained endotracheal tube is continuously curved, and preferably under flexural tension, from the most proximal location where the handle contacts the retained endotracheal tube to the most distal location where the insertion section contacts the superior side of a retained endotracheal tube.

40 Claims, 10 Drawing Sheets

(56) References Cited

U.S. PATENT DOCUMENTS

| | | | |
|---|---|---|---|
| 3,926,196 A | | 12/1975 | Bornhorst et al. |
| 3,943,920 A | * | 3/1976 | Kandel .................. 600/190 |
| 4,054,135 A | * | 10/1977 | Berman ................ 128/200.26 |
| 4,067,331 A | * | 1/1978 | Berman ................ 128/200.26 |
| 4,211,234 A | | 7/1980 | Fisher |
| 4,306,547 A | | 12/1981 | Lowell |
| 4,338,930 A | | 7/1982 | Williams |
| 4,612,927 A | | 9/1986 | Krüger |
| 4,832,020 A | | 5/1989 | Augustine |
| 4,947,896 A | | 8/1990 | Bartlett |
| 5,024,218 A | | 6/1991 | Ovassapian et al. |
| 5,038,766 A | | 8/1991 | Parker |
| 5,042,469 A | * | 8/1991 | Augustine ............. 128/200.26 |
| 5,065,738 A | * | 11/1991 | Van Dam .................. 600/185 |
| 5,203,320 A | | 4/1993 | Augustine |
| 5,261,392 A | | 11/1993 | Wu |
| 5,339,805 A | | 8/1994 | Parker |
| 5,349,943 A | | 9/1994 | Ruiz |
| 5,645,519 A | | 7/1997 | Lee et al. |
| 5,651,761 A | | 7/1997 | Upsher |
| 5,702,351 A | * | 12/1997 | Bar-Or et al. ............. 600/190 |
| 5,800,342 A | | 9/1998 | Lee et al. |
| 5,840,013 A | | 11/1998 | Lee et al. |
| 5,850,832 A | * | 12/1998 | Chu .................... 128/200.26 |
| 5,993,383 A | * | 11/1999 | Haase .................... 600/191 |
| 6,142,144 A | | 11/2000 | Pacey |
| 6,231,505 B1 | | 5/2001 | Martin |
| 6,471,643 B1 | | 10/2002 | Henderson |
| 6,655,377 B2 | | 12/2003 | Pacey |
| 7,182,728 B2 | * | 2/2007 | Cubb et al. ............... 600/194 |
| 7,946,981 B1 | * | 5/2011 | Cubb ..................... 600/194 |
| 8,079,951 B2 | | 12/2011 | Yokota |
| 8,202,215 B2 | * | 6/2012 | Xiao et al. ............... 600/194 |
| 8,479,625 B2 | * | 7/2013 | Klepper ................... 83/39 |
| 8,814,786 B2 | * | 8/2014 | Young et al. ............. 600/188 |
| 2002/0117171 A1 | * | 8/2002 | Parker .................. 128/200.26 |
| 2003/0168059 A1 | | 9/2003 | Pacey |
| 2005/0090712 A1 | | 4/2005 | Cubb |
| 2005/0133038 A1 | * | 6/2005 | Rutter .................. 128/207.17 |
| 2005/0240081 A1 | | 10/2005 | Eliachar |
| 2006/0276694 A1 | | 12/2006 | Acha Gandarias |
| 2008/0185004 A1 | * | 8/2008 | Munn ................. 128/207.14 |
| 2009/0032016 A1 | * | 2/2009 | Law et al. .............. 128/200.26 |
| 2010/0004514 A1 | * | 1/2010 | Shalman et al. ............ 600/187 |
| 2010/0211632 A1 | | 8/2010 | Saarinen |
| 2010/0256451 A1 | | 10/2010 | McGrath et al. |
| 2011/0270038 A1 | * | 11/2011 | Jiang et al. ................ 600/188 |
| 2012/0059223 A1 | | 3/2012 | McGrath et al. |
| 2012/0095294 A1 | | 4/2012 | McGrath et al. |
| 2012/0095295 A1 | | 4/2012 | McGrath et al. |
| 2013/0057667 A1 | | 3/2013 | McGrath |
| 2013/0060089 A1 | | 3/2013 | McGrath et al. |
| 2013/0060090 A1 | | 3/2013 | McGrath et al. |
| 2013/0066152 A1 | * | 3/2013 | Chen ..................... 600/188 |
| 2013/0267780 A1 | * | 10/2013 | Herrmann et al. .......... 600/157 |
| 2013/0345518 A1 | * | 12/2013 | Law et al. ................ 600/188 |
| 2014/0121463 A1 | | 5/2014 | McGrath et al. |
| 2014/0128681 A1 | * | 5/2014 | Fordinal ................. 600/194 |

FOREIGN PATENT DOCUMENTS

| | | |
|---|---|---|
| EP | 1 640 033 | 3/2006 |
| GB | 2431539 | 4/2007 |
| GB | 2 452 402 | 3/2010 |
| JP | 64-015062 | 1/1989 |
| JP | 2004-504919 | 2/2004 |
| JP | 2006-518621 | 8/2006 |
| JP | 2006-326111 | 12/2006 |
| JP | 2007-117116 | 5/2007 |
| WO | WO 80/00538 | 4/1980 |
| WO | WO 99/27840 | 6/1999 |
| WO | WO 01/10293 | 2/2001 |
| WO | 0211608 | 2/2002 |
| WO | WO 2004/008951 | 1/2004 |
| WO | WO 2004/073510 | 9/2004 |
| WO | WO 2005/107575 | 11/2005 |
| WO | 2007070944 | 6/2007 |

OTHER PUBLICATIONS

Japanese Examination Report dated Jan. 22, 2013 (with English translation) for corresponding Japanese Application No. 2010-522435 (9 pages).

Aircraft Medical v. King Systems Corp. et al., Claim No. CC13P00202, Patents County Court, United Kingdom, Initial pleadings of the case: Jan. 15, 2013 Claim Form, Particulars of Claim, Particulars of Infringement with Annexes A-D (72 pages).

Aircraft Medical v. King Systems Corp. et al., Claim No. CC13P00202, Patents County Court, United Kingdom—Defence and Counterclaim (Mar. 14, 2013), with Annexes 1-9 (111 pages).

Aircraft Medical v. King Systems Corp. et al., Claim No. CC13P00202, Patents County Court, United Kingdom—Reply and Defence to Counterclaim (Apr. 10, 2013), with Annexes E-I (31 pages).

Aircraft Medical v. King Systems Corp. et al., Claim No. CC13P00202, Patents County Court, United Kingdom—Application Notice (Apr. 10, 2013), with Draft Order on Amendment to the Patent and Statement of Reasons (Apr. 10, 2013) and Annexes 1 and 2 (73 pages).

Aircraft Medical v. King Systems Corp. et al., Claim No. CC13P00202, Patents County Court, United Kingdom—Reply to Defence to Counterclaim and Notice of Opposition to Proposed Amendments (May 15, 2013) and Annexes 10-13 (49 pages).

Aircraft Medical v. King Systems Corp. et al., Claim No. CC13P00202, Patents County Court, United Kingdom—Letter from UKIPO dated Jun. 4, 2013, re Application for Amendment (3 pages).

C. H. Maharaj et al., "Evaluation of intubation using the Airtraq® or Macintosh laryngoscope by anaesthetists in easy and simulated difficult laryngoscopy—a manikin study," Anaesthesia, 2006, 61, pp. 469-477.

C. H. Maharaj et al., "Learning and performance of tracheal intubation by novice personnel: a comparison of the Airtraq® and Macintosh laryngoscope," Anaesthesia, 2006, 61, pp. 671-677.

Benumof's Airway Management: Principles and Practice, 2d Ed., Edited by Carin A. Hagberg, MD, Mosby Elsevier, 2007, pp. 559-560.

Mercury Medical Brochure, "Introducing . . . The CookGas® ILA—Intubating Laryngeal Airway and Removal Stylet," Jun. 2006, pp. 1-41.

UK Search Report for UK Application No. GB0716613.5, dated Dec. 20, 2007.

UK Search Report for UK Application No. UKGB0716668.9, dated Dec. 20, 2007.

UK Search Report for UK Application No. GB0716671.3, dated Dec. 28, 2007.

UK Search Report for UK Application No. GB0716615.0, dated Jun. 27, 2008.

UK Search Report for UK Application No. GB0716667.1, dated Jun. 27, 2008.

UK Search Report for UK Application No. GB0716612.7, dated Jun. 27, 2008.

UK Search Report for UK Application No. GB0815663.0, dated Nov. 19, 2008.

UK Search Report for UK Application No. GB0815656.4, dated Nov. 19, 2008.

UK Search Report for UK Application No. GB0815658.0, dated Nov. 19, 2008.

UK Search Report for UK Application No. GB0815659.8, dated Nov. 19, 2008.

UK Search Report for UK Application No. GB0815660.6, dated Nov. 19, 2008.

UK Search Report for UK Application No. GB0815661.4, dated Nov. 19, 2008.

UK Search Report for UK Application No. GB0815662.2, dated Nov. 19, 2008.

International Search Report for International Application No. PCT/GB2008/002900, dated May 14, 2009.

(56) References Cited

OTHER PUBLICATIONS

Office Action (12 pgs.) dated Apr. 23, 2014 issued in co-pending U.S. Appl. No. 14/073,380.
Apr. 22, 2015 Office Action issued in U.S. Appl. No. 14/073,380.
Dec. 31, 2014 Office Action issued in U.S. Appl. No. 14/073,380.
Jul. 29, 2014 Office Action issued in U.S. Appl. No. 14/073,380.
Japanese Examination Report dated Apr. 5, 2013 (with English translation) for Japanese Application No. 2010-522434.

* cited by examiner

LARYNGOSCOPE

This application is the U.S. National Phase of International Application No. PCT/GB2008/002903, filed 28 Aug. 2008, which designated the U.S. and claims priority to Great Britain Application No. 0716672.1, filed 28 Aug. 2007 the entire contents of each of which are hereby incorporated by reference.

FIELD OF THE INVENTION

The present invention relates to the field of laryngoscopes having insertion sections which include tube guides.

BACKGROUND TO THE INVENTION

Laryngoscopes are in common use for the insertion of endotracheal tubes into the tracheas of patients during medical procedures. Laryngoscopes comprise a handle which remains outside the patient's oral cavity, for manoeuvring the laryngoscope during a procedure, and an insertion section which is extended into a patient's oral cavity, towards the larynx, in use. A light source and imaging apparatus, such as a series of mirrors and/or prisms, or a video camera, are provided towards the distal end of the insertion section to enable the patient's trachea to be viewed by a user during the intubation procedure. The insertion section may be an integral part of the laryngoscope or detachably retainable on a laryngoscope body portion which comprises the handle. A laryngoscope or detachably retainable insertion section may be reusable or disposable. Reusable video camera apparatus may be used with a reusable or disposable laryngoscope body portion and a reusable or disposable insertion section. A laryngoscope, including video camera apparatus, may be entirely disposable.

Within this specification and the appended claims, the inferior surface is the surface of an insertion section which faces the patient's tongue in use. The opposite surface is referred to as the superior surface. Words such as inferior, inferiorly, superior and superiorly are used in corresponding senses. The words distal and distally refer to being towards the end of the insertion section which extends towards a patient's trachea in use and the words proximal and proximally refer to being towards the person carrying out intubation in use.

In order to carry out intubation by traditional methods, using a traditional laryngoscope, such as a Macintosh laryngoscope, an intubater holds the laryngoscope in one hand and a sterile endotracheal tube in the other hand. Endotracheal tubes typically include a gentle curve and the tube is orientated to curve in the same sense as the patient's airway. The laryngoscope is then inserted into a patient. Once sight of the larynx has been achieved, the endotracheal tube is inserted using the other hand, along the curved arc of the tube. This two step procedure, requiring insertion of the laryngoscope and then an endotracheal tube, has been used successfully for many years, but it would be preferable to reduce the manual complexity of the task to facilitate rapid intubation.

It has been proposed to provide laryngoscopes which include a tube guide which can detachably retain and guide an endotracheal tube whilst the insertion section is introduced into a patient's airway. For example, WO 04/073510 (Gandarias) discloses a laryngoscope insertion section having a tube guide which extends laterally from an elongate member which contains apparatus to provide an image of a patient's larynx in use. Once the laryngoscope is in place and a clear view of the larynx has been obtained, an endotracheal tube within the guide is advanced into a patient's larynx whilst the larynx and advancing tube are monitored visually. The endotracheal tube can then be detached from the insertion section whilst the insertion section remains within a patient and the insertion section can be removed, leaving the endotracheal tube in place.

An advantage of providing a tube guide which can retain and guide an endotracheal tube is that the endotracheal tube is introduced into the airway at the same time as the laryngoscope, potentially speeding up intubation. Conceivably, a nurse or other member of support staff could insert the endotracheal tube into the tube guide and hand the laryngoscope with retained tube guide to the intubater, or leave it where the intubater can readily pick it up, speeding up intubation. However, with the laryngoscope disclosed in WO 04/073510, the proximal end of an endotracheal tube (i.e. the end which will remain outside a patient's airway in use) is not controlled, increasing the overall volume occupied by the laryngoscope and retained endotracheal tube and presenting a cumbersome appearance.

A further disadvantage of the laryngoscope disclosed in WO 04/073510 is that the proximal end of a retained endotracheal tube, which is not retained within the tube guide, is displaced laterally by the handle, bending the endotracheal tube laterally and increasing the difficulty of inserting the endotracheal tube.

As the endotracheal tube is retained in a deep groove throughout the tube guide, so that the endotracheal tube is not exposed on the surface of the tube guide, it can only be manipulated by grabbing the proximal end and pushing the tube. Thus, only a limited amount of control is possible. This problem is compounded in the laryngoscope disclosed in U.S. Pat. No. 6,655,377 (Saturn Biomedical), which has a handle that engages with a received endotracheal tube by including a straight through-bore through which a retained endotracheal tube extends in use. The endotracheal tube within the handle is not exposed on the surface of the handle and an intubater must reach quite far back, proximally of the handle, to manipulate a retained endotracheal tube.

Furthermore, known laryngoscopes with tube guides retain an endotracheal tube in a generally J-shaped configuration. This has two significant disadvantages. Firstly, the insertion of a J-shaped insertion section into a patient's oral cavity is reasonably difficult. A J-shaped insertion section normally must be tilted backwards and forwards during insertion to insert the distal end, manipulate the patient's anatomy and obtain a good view of the patient's larynx. It is preferable to provide a laryngoscope which can be more readily inserted. Secondly, this arrangement means that, when the endotracheal tube is pushed forward to advance the tube, a force is developed on the superior side of the tube guide where the endotracheal tube bends from being substantially straight to curved, which increases friction.

A still further disadvantage of known laryngoscopes with J-shaped insertion sections is that the method of inserting the laryngoscope and advancing the endotracheal tube is quite different to the traditional methods employed by intubaters using generally curved insertion sections that do not require multiple positioning manoeuvres which leave the intubater's other hand free to manoeuvre the endotracheal tube. It would be preferable to provide a laryngoscope including a tube guide which enabled intubaters to transfer the skills they have learned when using traditional laryngoscopes, such as Macintosh laryngoscopes, such as the hand motion required to move a curved tube along the curved path of a tube.

Accordingly, the invention aims to provide an improved laryngoscope which reduces or avoids one or more of the abovementioned disadvantages of known laryngoscopes.

SUMMARY OF THE INVENTION

According to a first aspect of the present invention there is provided a laryngoscope comprising a handle and an insertion section which extends from the handle, wherein the insertion section comprises a tube guide for retaining and guiding an endotracheal tube during intubation, wherein the handle comprises at least one external tube engaging formation.

As the handle comprises at least one external tube engaging formation, rather than a through-bore or a narrow, deep channel retaining an endotracheal tube within the body of the handle, the laryngoscope is easier to use than a laryngoscope having a through-bore or a narrow, deep channel retaining an endotracheal tube within the body of the handle.

By an endotracheal tube, we refer to an endotracheal tube suitable for use with the laryngoscope. An endotracheal tube suitable for use with the laryngoscope will have an external diameter which depends on the patients which the laryngoscope has been adapted to intubate. The range of external diameters of endotracheal tubes that are suitable for use with the laryngoscope is referred to herein as the operating range of endotracheal tube external diameters.

For example, a laryngoscope for use with adult humans may, for example, be adapted for use with endotracheal tubes having a minimum external diameter of around 5.5 mm. It may be possible to fit a smaller external diameter endotracheal tube, for example a 1 mm external diameter endotracheal tube intended for use with newborn infants, into the tube guide, however such a tube would not be suitable for use with a laryngoscope for use with adult humans and so does not have an external diameter within the operating range of endotracheal tube external diameters. A laryngoscope for use with adult humans may, for example, be adapted for use with endotracheal tubes having a maximum external diameter of around 12.3 mm. Endotracheal tubes which have an external diameter in excess of the upper end of external diameter in the operating range of endotracheal tube external diameters may not fit into the tube guide, not be usable without substantial friction or have dimensions which are inappropriate to patients having the dimensions for which the laryngoscope was designed.

In the case of a laryngoscope for inserting endotracheal tubes into infant humans, including new born infants, the operating range of external tube diameters may, for example, be from around 1.0 to around 5.0 mm. The dimensions of a laryngoscope for use with infant humans, including new born infants, are typically scaled proportionately from the dimensions of an insertion section for use with human adults. Nevertheless, the proportions of some features, such as the thickness of the tube guiding members or the dimensions of the handle may not scale proportionately.

At least one external tube engaging formation may be a tube retaining member arranged to detachably retain on the handle an endotracheal tube which is received by the tube guide. By "retain on the handle" we mean that at least a surface of a retained endotracheal tube is on the surface of the handle. An endotracheal tube recessed entirely within a groove which is deeper than the diameter of the endotracheal tube and not substantially broader than the diameter of the endotracheal tube is not on the handle. The tube retaining member may be suitable for detachably retaining endotracheal tubes with external diameters at the upper end of (and preferably also the middle, or most preferably also the lower end of) the operating range of endotracheal tube external diameters on the surface of the handle.

At least one external tube engaging formation may be a tube guiding member arranged to guide along the handle an endotracheal tube which is received within the tube guide. By "guide along the handle" we mean that at least a surface of a retained endotracheal tube extends along and is guided along at least a length of the surface of the handle. An endotracheal tube recessed entirely within a groove which is deeper than the diameter of the endotracheal tube and not substantially broader than the diameter of the endotracheal tube does not extend along the handle. The tube guiding member may be suitable for guiding endotracheal tubes with external diameters at the upper end of (and preferably also the middle, or most preferably also the lower end of) the operating range of endotracheal tube external diameters along the surface of the handle.

By "the tube guide" we refer to the tube guide which is part of the insertion section, which functions to retain and guide an endotracheal tube, and not any tube guiding member which is part of the handle.

Both at least one tube guiding member and at least one tube retaining member may be provided. At least one external tube engaging formation may function as both a tube guiding member and a tube retaining member.

Preferably, the at least one tube engaging formation is arranged such that a retained and/or guided endotracheal tube (for example, an endotracheal tube with an external diameter at the upper end of, and preferably also at the middle of, and most preferably also at the lower end of, the operating range of endotracheal tube external diameters), may be contacted by, and preferably at least slightly pinched by, a user where the endotracheal tube is retained on and/or guided along the handle.

Preferably also, the at least one tube engaging formation is arranged such that a retained and/or guided endotracheal tube (for example, an endotracheal tube with an external diameter at the upper end of, and preferably also at the middle of, and most preferably also at the lower end of, the operating range of endotracheal tube external diameters) may be contacted by, and preferably at least slightly pinched by, a user where the endotracheal tube is retained on and/or guided along the handle, whilst the user grips the handle.

The ability to physically contact the endotracheal tube where the retained endotracheal tube is retained on and/or guided along the handle, improves the manual control of the tube available to the intubater. By "pinch" we refer to the possibility of at least slightly distorting the endotracheal tube by pressing it with a finger or the palm of the hand, thereby facilitating better control of the endotracheal tube.

Preferably, the insertion section is arranged so that an intubater can contact an endotracheal tube retained by the tube guide within a patient's mouth, in use. This increases the amount of control which is available to the intubater and may be preferred by intubaters who have been trained to carry out intubation using traditional laryngoscopes, who are used to being able to manipulate the endotracheal tube within the patient's mouth. The insertion section may comprise a proximal superior tube guiding member having a tube guiding surface arranged to contact and thereby guide the superior surface of an endotracheal tube retained in the tube guide and the insertion section may be arranged so that an intubater can contact an endotracheal tube retained within the tube guide within a patient's mouth, in use, distally of the tube guiding surface of the proximal superior tube guiding member. The insertion section may be arranged to that an intubater can contact one or more of the inferior or superior surfaces of an endotracheal tube retained within the tube guide within a patient's mouth, in use (e.g. distally of the distally of the tube guiding surface of the proximal superior tube guiding member, where present). The insertion section may be arranged to that an intubater can contact a lateral surface of an endotracheal tube retained within the tube guide within a patient's mouth, in use (e.g. distally of the distally of the tube guiding surface of the proximal superior tube guiding member, where present). The insertion section may be arranged so that an intubater can contact opposite inferior and superior surfaces of the endotracheal tube within a patient's mouth, in use, (e.g. distally of the distally of the tube guiding surface of the proximal superior tube guiding member, where present), to facilitate grip and enable them to gently pinch the tube.

At least one tube guiding member may comprise a groove on the external surface of the handle of the laryngoscope. By a groove we refer to either an elongate open recess or an elongate open channel between elongate raised surfaces. Where the groove is in the form of an elongate recess, the cross-section of the laryngoscope handle may be reduced or, where the shape of the laryngoscope handle is dictated by ergonomic considerations, the outer surface handle may more closely conform to a shape which is selected for ergonomic reasons.

At least one tube guiding member may comprise an elongate guide wall on the external surface of the handle of the laryngoscope, for contacting and thereby guiding an endotracheal tube in use. An elongate guide wall is typically generally parallel to the length of the handle. An elongate recess may be provided adjacent the elongate guide wall, so that the recess and guide wall together guide an endotracheal tube.

Preferably, the at least one tube engaging member is configured so that a retained endotracheal tube (for example, an endotracheal tube with an external diameter at the upper end of, and preferably also at the middle of, and most preferably also at the lower end of, the operating range of endotracheal tube external diameters) remains at least partially exposed along at least the majority of and preferably all of the length of the handle.

Preferably, the at least one tube engaging member is configured so that either the most inferior or most superior point on the surface of a retained endotracheal tube (for example, an endotracheal tube with an external diameter at the upper end of, and preferably also at the middle of, and most preferably also at the lower end of, the operating range of endotracheal tube external diameters) remains exposed along at least the majority of, and preferably all of, the length of the handle.

Where the tube guiding member comprises a groove, the groove is configured so that an endotracheal tube (for example, an endotracheal tube with an external diameter at the upper end of, and preferably also at the middle of, and most preferably also at the lower end of, the operating range of endotracheal tube external diameters) guided in the groove extends at least partially, and preferably predominantly, out of the groove along the length of the groove. The depth of the groove may vary along the length of the groove. For example, the groove may have relatively shallow ends with a relatively deep section therebetween. Where the groove is an elongate recess in the surface of the handle, a guided endotracheal tube will therefore extend at least partially, and preferably predominantly, out from the surrounding surface of the handle. The groove may have a rounded profile.

In the case of a laryngoscope for the intubation of adult humans, the depth of the groove, at its deepest point, is preferably less than 6 mm and more preferably less than 4 mm. In an endotracheal tube for the intubation of human infants, including newborn infants, the depth of the groove, at its deepest point, is preferably less than 1 mm.

Where the tube guiding member comprises an elongate guide wall, the guide wall typically has a height equal to at least half of the lower end of the operating range of endotracheal tube external diameters. The guide wall may, however, have a height which is greater than the upper end of the operating range of endotracheal tube external diameters.

Where at least one tube retaining member is provided, the at least one tube retaining member is preferably arranged to detachably retain (and, where the tube retaining member also functions as a tube guiding member, to guide) an endotracheal tube which is received within the tube guide. Thus, a nurse or other member of support staff may fit an endotracheal tube into the tube guide and retain it on the handle using the at least one tube retaining member. They might then pass the laryngoscope and retained endotracheal tube to an intubater, or leave it where the intubater can pick up the laryngoscope and retained endotracheal tube. Preferably, the endotracheal tube can be detached from the at least one tube retaining member without the endotracheal tube being advanced or withdrawn within the tube guide.

Preferably, a retained endotracheal tube can be detached from the at least one tube retaining member without removing the retained endotracheal tube from the tube guide, such that the retained endotracheal tube is fully exposed proximally of the most proximal part of the insertion section which contacts the retained endotracheal tube.

The at least one tube retaining member is preferably arranged to detachably retain (and, where the tube retaining member also functions as a tube guiding member, to guide) an endotracheal tube which is received with the tube guide, the at least one tube retaining member is preferably adapted so that a detachably retained endotracheal tube can be detached from the laryngoscope in situ, within a patient, before the laryngoscope is removed. Preferably, a retained endotracheal tube can be detached by displacing the retained endotracheal tube generally laterally relative to the laryngoscope.

The at least one tube retaining member may comprise a tube retaining surface, such as a tube retaining surface of a tube retaining protrusion or, where the handle is bent, a portion of the handle. The at least one tube retaining surface (e.g. a tube retaining surface of a tube retaining protrusion) may be located on the handle at a location such that an endotracheal tube brought into tube retaining contact with at least one tube retaining surface is retained by virtue of flexural tension in the endotracheal tube. Endotracheal tubes are typically inherently curved. Accordingly, the at least one tube retaining surface is typically located such that a tube received within the tube guide of the insertion section has to be curved by more than its integral curvature to be brought into tube retaining contact with the at least one tube retaining surface.

By retaining an endotracheal tube in flexural tension proximally of the insertion section tube guide, retention of the endotracheal tube is facilitated. This is especially relevant where the endotracheal tube can be detached from the laryngoscope in a generally lateral direction.

The at least one tube retaining surface may be arranged to detachably retain an endotracheal tube without guiding the endotracheal tube. For example, the at least one tube retaining surface may be smooth, such as a smooth surface of a protrusion which extends from the handle. Alternatively, the at least one tube retaining surface may define a tube guiding formation, such as a groove, for example, a recess. For example, the at least one tube retaining surface may be a generally smooth surface, such as a smooth surface of a protrusion which extends from the handle, including a recess which functions to guide a retained endotracheal tube.

By providing a handle with least one tube retaining member, an endotracheal tube is retained proximally of the insertion section. This improves control of the retained endotracheal tube in comparison with a laryngoscope which does not retain an endotracheal tube proximally of the insertion section. It can also reduce the overall bulk of the laryngoscope and retained endotracheal tube and provide a less cumbersome appearance.

Typically, the tube retaining member comprises at least one tube retaining protrusion which protrudes from the handle. More preferably, the at least one tube retaining protrusion protrude laterally from the handle.

The at least one tube retaining protrusion may comprise a video screen support for displaying images received from a video camera, which is located within or attached to the insertion section, which video screen support protrudes from the handle. Accordingly, the laryngoscope handle may comprise a video screen support which protrudes from the handle and functions as a tube retaining protrusion. The video screen support may comprise a tube retaining surface which comprises a groove for guiding a retained endotracheal tube.

The at least one tube retaining protrusion may comprise a clip, such as a clip which extends partially around a retained endotracheal tube, or at least partially across a groove for guiding an endotracheal tube. A clip may be provided which engageably extends around a retained endotracheal tube.

At least one of the tube engaging members is typically located within, or extends into, the proximal half of the length of the handle, more preferably within the most proximal quarter of the length of the handle and most preferably within the most proximal 10% of the length of the handle.

Preferably, at least one of the tube engaging members which functions as a tube retaining member (and optionally also as a tube guiding member) is typically located within, or extends into, the proximal half of the length of the handle, more preferably within the most proximal quarter of the length of the handle and most preferably within the most proximal 10% of the length of the handle. This provides better control of the proximal end of the endotracheal tube.

At least one tube engaging formation may comprise a tube guiding member which protrudes from the handle to contact the inferior or superior surface of a retained endotracheal tube. At least one said tube guiding members may be provided adjacent to a groove. At least one said tube guiding members may have an incurvate tube contacting surface to retain and guide an endotracheal tube.

The laryngoscope may be arranged to keep an endotracheal tube retained in the tube guide continuously curved (preferably curved by more than its integral curvature) from the most proximal location where the laryngoscope contacts a retained endotracheal tube to the most distal location where the laryngoscope contacts the superior surface of retained endotracheal tube. This facilitates intubation as the endotracheal tube can be easier to guide into a patient's trachea where it is curved along the length of the tube guide. This arrangement also reduces friction in comparison to a J-shaped tube guide. Furthermore, the hand motion required to move a curved tube along the curved path of the tube corresponds to the hand motion which takes place when inserting an endotracheal tube using a conventional (e.g. Macintosh) laryngoscope, enabling an intubater to use similar skills to those developed with conventional laryngoscopes.

In order to facilitate the retention of an endotracheal tube along a curved path and to facilitate intubation, the insertion section is preferably continuously curved at least from the proximal location where it contacts a retained endotracheal tube to the most distal location where it contacts the superior side of a retained endotracheal tube. The curvature may be constant or vary along the curved path.

Preferably, the laryngoscope is arranged such that (in the case of a laryngoscope for use in the intubation of adults), the straight line distance from the most proximal location where the laryngoscope contacts a retained endotracheal tube to the most distal location where the laryngoscope contacts the superior side of a retained endotracheal tube is at least 200 mm, more preferably 220 to 240 mm. This maximises the distance along which a retained endotracheal tube is maintained in a continuous curve. Proportionately smaller sizes could be employed for use with human infants.

Preferably, the laryngoscope is arranged such that a retained endotracheal tube, of at least one external diameter (typically the largest diameter in an operating range of external diameters, e.g. 12.3 mm in the case of a laryngoscope for use in the intubation of adults) is curved by at least 90°, and preferably at least 100°, at least 115° or at least 135° between the most proximal location where the laryngoscope contacts a retained endotracheal tube and the most distal location where the laryngoscope contacts the superior side of a retained endotracheal tube. This maximises the arc along which a retained endotracheal tube is maintained in a continuous curve. The laryngoscope may contact the superior surface of a retained endotracheal tube at most proximal location where the laryngoscope contacts a retained endotracheal tube.

Preferably, the laryngoscope is arranged to retain an endotracheal tube under flexural tension from the most proximal location where the tube guide contacts a retained endotracheal tube to the most distal location where the tube guide contacts the superior surface of a retained endotracheal tube. Preferably, the laryngoscope is arranged to retain an endotracheal tube under flexural tension from the most proximal location where the tube guide contacts the superior surface of a retained endotracheal tube to the most distal location where the tube guide contacts the superior surface of a retained endotracheal tube. This facilitates retention of an endotracheal tube. This is of particular benefit where the insertion section tube guide is laterally opening and arranged to allow the removal of a retained endotracheal tube in a lateral direction, as it allows the number and size of tube guiding members which define the tube guide to be minimised, reducing the bulk of the insertion section. The tube guide may also be more open on its lateral side than would otherwise be the case. This is also of particular benefit where the endotracheal tube extends along a lateral side of the handle such that a retained endotracheal tube can be removed in a generally lateral direction.

Preferably, the laryngoscope (typically, the insertion section tube guide or a tube guiding member extending from the handle) also contacts the inferior surface of a retained endotracheal tube intermediate the most proximal and most distal locations where the tube guide contacts the superior surface of a retained endotracheal tube, such that a retained endotracheal tube exerts a superior force at the most proximal and most distal locations where the tube guide contacts the superior surface of a retained endotracheal tube and an inferior force at the said location where the tube guide contacts the inferior surface of a retained endotracheal tube. The use of at least three points of contact facilitates grip, resisting lateral movement. Preferably, the laryngoscope is arranged such that inferior and superior surfaces of endotracheal tubes with at least some external diameters in the operating range of external diameters contact the laryngoscope in at most four locations, and preferably at most three locations. This reduces friction when the endotracheal tube is advanced.

The laryngoscope may be arranged such that the path described by a retained endotracheal tube from the tube guide to the most proximal location where it contacts the handle has at least some lateral extent. However, the laryngoscope may be arranged such that the path described by a retained endotracheal tube from the tube guide to the most proximal location where it contacts the handle is substantially within a plane. This means that the retained endotracheal tube is curved in only one direction, reducing lateral bending forces and friction. Preferably, the laryngoscope may be arranged such that the path described by a retained endotracheal tube from the tube guide to the most proximal location where it contacts the handle is substantially parallel to the centre line of the laryngoscope. By the centre line we refer to the direction which will be in the midsagittal plane in use. This arrangement reduces the friction experienced by a retained endotracheal tube when it is advanced towards a patient's trachea and means that a relatively natural motion, similar to that used with conventional laryngoscopy, is employed to advance the retained endotracheal tube into a patient's trachea. This arrangement is of particular benefit where the endotracheal tube is retained on the outside of the handle enabling an intubater to conveniently touch and advance the endotracheal tube. The external surface of the handle may comprise a planar tube contacting surface which extends parallel to the centre line of the laryngoscope.

Preferably, the tube guide is arranged to hold a section of an endotracheal tube so that it extends along at least some, and preferably at least the majority, of the length of the insertion section. The tube guide is preferably a laterally opening tube guide from which a retained endotracheal tube may be removed in a generally lateral direction. Typically, the at least one tube engaging formation is provided on the side of the laryngoscope where the tube guide opens.

The insertion section preferably comprises an elongate member having a lateral tube guide extending laterally therefrom. Typically, the tube retaining formation is provided on the same side of the laryngoscope as the lateral tube guide.

The elongate member may comprise imaging apparatus, such as an imaging device (e.g. a camera) or image conduction apparatus (such as at least one fibre optic cable or at least one reflective surfaces) for imaging a patient's larynx in use. The elongate member may comprise illumination apparatus, such as a light source, including a bulb or at least one fibre optical cable through which light may be conducted, for illuminating a patient's laryngopharynx in use. The elongate member may conduct at least one cable therein, such as electrical wires which relay signals from an imaging device and/or provide power to an imaging device and/or light source, where present.

The elongate member may define a bore therein, which typically extends from the proximal end of the elongate member, which may be a through-bore or which may be enclosed at a distal end. The bore may be configured to receive imaging apparatus and/or illumination apparatus. The bore may be configured to receive an elongate insertion section retaining member which includes the imaging apparatus and/or illumination apparatus. Where the bore is enclosed at a distal end, the elongate member is preferably liquid tight to prevent contamination of imaging apparatus and/or illumination apparatus enclosed therein. The imaging apparatus and/or illumination apparatus and/or strengthening member are preferably attached to the body of the laryngoscope.

The elongate member may be adapted to removably retain imaging apparatus. Accordingly, the elongate member may be disposable but adapted to removably retain reusable imaging apparatus. Reusable imaging apparatus typically comprises a video camera (e.g. a CCD or CMOS video camera), a transmitter, which may be wired or wireless, for transmitting video signals to a receiver for use in displaying images during intubation, and a power supply, which may be a wired connection, a wireless power supply (for example, an inductive power transfer system) or a battery or capacitor.

Typically, the insertion section extends at an angle of at least 20°, and preferably at least 30°, and more preferably around 40° to the central axis of the handle.

Preferably, the handle has a proximal end, which is towards a user in use, and a distal end, and the insertion section extends from the distal end of the handle. Typically, the insertion section has a proximal end, towards the handle, and a distal end which extends into a patient's laryngopharynx in use. The tube guide typically extends distally from the proximal end of the insertion section. Typically, the insertion section has an inferior surface which is adapted for contact with a patient's tongue in use, and an opposed superior surface and the tube guide comprises inferior and superior tube guide walls which extend along the edge of at least a part of the inferior and superior surfaces of the tube guide. Preferably, the superior tube guide walls comprise separate proximal and distal portions.

The laryngoscope may be adapted to be used in a single intubation. Accordingly, the laryngoscope may comprise a handle, insertion section and imaging apparatus (such as a camera) which are adapted to be used in a single intubation. Thus, the laryngoscope may be entirely disposable.

According to a second aspect of the present invention there is provided a laryngoscope comprising a handle and an insertion section which extends from a distal end of the handle, the handle and insertion section being adapted to detachably retain and guide an endotracheal tube along a lateral side of the insertion section and handle such that a retained endotracheal tube is continuously curved from the most proximal location where the handle contacts the retained endotracheal tube to the most distal location where the insertion section contacts the superior side of a retained endotracheal tube.

Preferably, the insertion section and handle each comprise external tube guiding members which detachably retain and guide an endotracheal tube along a lateral side of the insertion section and handle such that a retained endotracheal tube is continuously curved from the most proximal location where the handle contacts the retained endotracheal tube to the most distal location where the insertion section contacts the superior side of a retained endotracheal tube.

Typically, the insertion section includes at least two external tube guiding members, one of which is arranged to contact and guide the superior surface of a received endotracheal tube and one or which is arranged to contact and guide the inferior surface of a received endotracheal tube, and the handle comprises at least one of the external tube guiding members.

Preferably, the laryngoscope is arranged such that, for endotracheal tubes with a range of external diameters within the operating range of endotracheal tube external diameters, a retained endotracheal tube is held in flexural tension from the most proximal location where the laryngoscope contacts a retained endotracheal tube to the most distal location where the insertion section contacts the superior surface of a retained endotracheal tube.

Preferably, the laryngoscope is arranged such that, for endotracheal tubes with a range of external diameters within the operating range of endotracheal tube external diameters, a retained endotracheal tube is held in flexural tension from the most proximal location where the laryngoscope contacts the superior surface of a retained endotracheal tube to the most distal location where the insertion section contacts the superior surface of a retained endotracheal tube.

Preferably, the most proximal location where the laryngoscope contacts a retained endotracheal tube (and preferably also the most proximal location where the laryngoscope contacts the superior surface of a retained endotracheal tube) is in the proximal half (preferably the proximal quarter by length and most preferably the most proximal 10% by length).

Preferably, the tube guiding members are arranged to enable a retained endotracheal tube to be separated from the handle and insertion section within a patient without the laryngoscope being withdrawn.

At least one tube guiding member may comprise a groove.

At least one tube guiding member of the insertion section may constitute a tube guide according to the first aspect of the invention. At least one tube guiding member of the handle may constitute an external tube engaging formation according to the first aspect of the present invention which functions as both a tube guiding member and a tube retaining member. Further preferred features of the second aspect of the invention correspond to those discussed above in relation to the first aspect of the invention.

Thus, the invention extends in a third aspect to a kit of parts comprising a insertion section and a laryngoscope body which comprises a handle, wherein the laryngoscope body and the insertion section comprise co-operating formations to enable the insertion section to be removeably attached to the body, wherein the insertion section comprises a tube guide for retaining and guiding an endotracheal tube during intubation and the handle comprises at least one tube engaging formation, the laryngoscope body and insertion section being arranged to form a laryngoscope according to the first or second aspect of the invention when the insertion section is removeably attached to the body.

The co-operating formations may comprise an elongate insertion section retaining member which extends from the handle of the laryngoscope body and a bore within the insertion section which is adapted to removeably receive the elongate insertion section retaining member. The elongate insertion section retaining member may comprise optical apparatus adapted to enable a user to view a patient's trachea in use, for example a light source and video camera. The insertion section may be disposable.

Further optional features correspond to those discussed above in relation to the first aspect of the invention.

According to a fourth aspect of the present invention, there is provided a method of preparing a laryngoscope for an intubation procedure, comprising fitting an endotracheal tube to the tube guide of a laryngoscope according to the first aspect of the present invention and engaging the tube guide with the at least one tube engaging formations of the laryngoscope body.

Where the laryngoscope is a laryngoscope according to the first aspect of the present invention, at least one of the external tube engaging formations is preferably a tube guiding member. The method will typically further comprise replacing the insertion section with an alternative disposable insertion section before carrying out a further intubation. Alternatively, multiple intubations may be carried out using new, typically sterilised, laryngoscopes.

According to a fifth aspect of the present invention, there is provided a method of preparing a laryngoscope for an intubation procedure, comprising fitting an endotracheal tube to the tube guide of a laryngoscope according to the second aspect of the present invention and engaging the tube guide with the plurality of tube guiding members.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
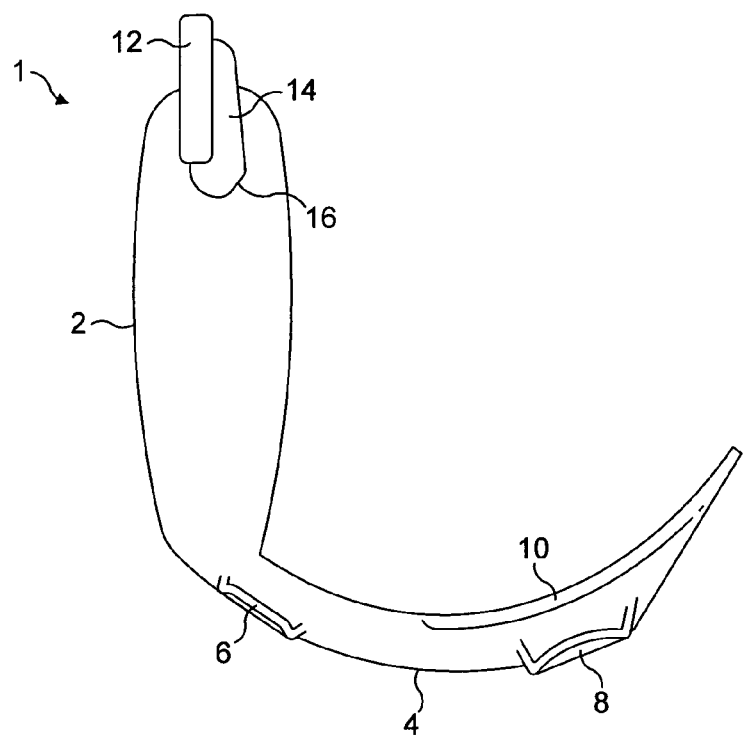
FIG. 1 is a lateral view of a laryngoscope, without a retained tube.

With reference to FIG. 1, a laryngoscope shown generally as 1 comprises an elongate handle 2, which is ergonomically shaped to facilitate grip by a user, and an elongate disposable insertion section 4, which is removeably attachable to the handle. The disposable insertion section includes an elongate lateral tube guide which is arranged to retain an endotracheal tube along the majority of the side of the insertion section and which is defined by a proximal superior tube guide portion 6, a distal superior tube guide portion 8, and an inferior tube guide portion 10. A video screen 12 is supported by a video screen retaining arm 14 which protrudes laterally from the handle. The underside of the video screen 16 is smooth.

The body of the laryngoscope includes a protrusion (not shown) which fits demountably into a bore (not shown) which runs within the insertion section. The protrusion supports a light source and video camera at the distal end thereof (not shown). Cables running along the length of the protrusion provide power to the light source and the camera and relay data signals back to the handle. The insertion section is at least partially transparent to enable the video camera to observe images viewed through the insertion section. In use, the video screen displays images observed by the video camera.

Figure 2:
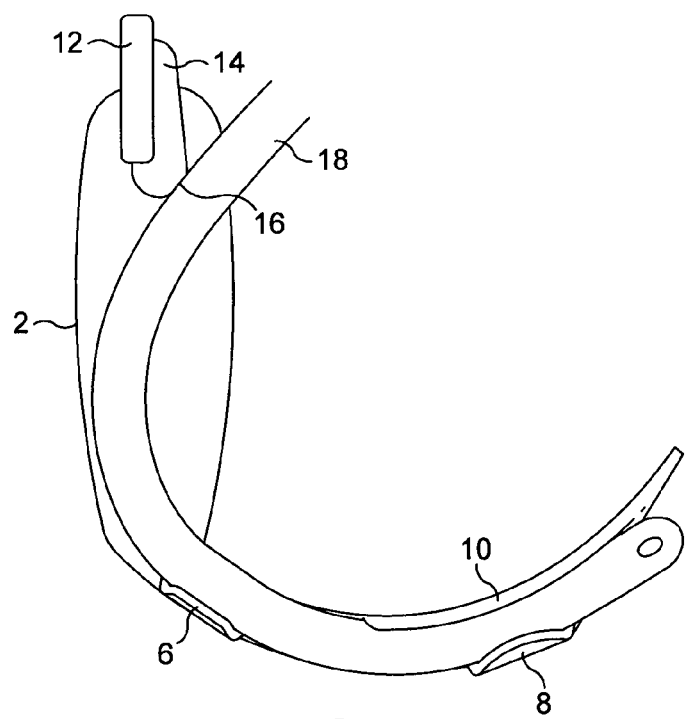
FIG. 2 is a lateral view of the laryngoscope of FIG. 1, with a retained tube.

FIG. 2 illustrates the same laryngoscope retaining an endotracheal tube 18. The endotracheal tube is fitted so that it is retained by the protruding video screen retaining arm, which functions as a tube retaining member. Although the endotracheal tube is inherently curved, it is bent by more than its natural curvature and so, as the endotracheal tube is resilient, it is retained by the resulting force between the video screen retaining arm and the bent tube. Accordingly, the retained endotracheal tube is in flexural tension from the most proximal location where it contacts the laryngoscope to the most distal location where the laryngoscope contacts the superior surface of the endotracheal tube. The retained endotracheal tube is curved between where it contacts the video screen retaining arm (the most proximal location where the laryngoscope contacts the superior surface of a retained endotracheal tube) and the distal superior tube guiding portion (the most distal location where the laryngoscope contacts the superior surface of a retained endotracheal tube). Because the endotracheal tube remains curved, the resistance of friction to insertion of the endotracheal tube into a patient's trachea is reduced. However, the retained endotracheal tube is curved such that it remains within a plane, which is parallel to a patient's midsagittal plane in use, and does not curve laterally. Accordingly, the retained endotracheal tube is advanced into a patient generally along its own curved path. Not only is this a natural movement for an intubator who is trained using conventional laryngoscopes, the avoidance of lateral curvature reduces friction.

The video camera and light source facilitate the insertion of an endotracheal tube which is retained in the guide into a patient's trachea. After intubation, the endotracheal tube can be displaced laterally from the tube guide and separated from the insertion section within a patient.

Figure 3:
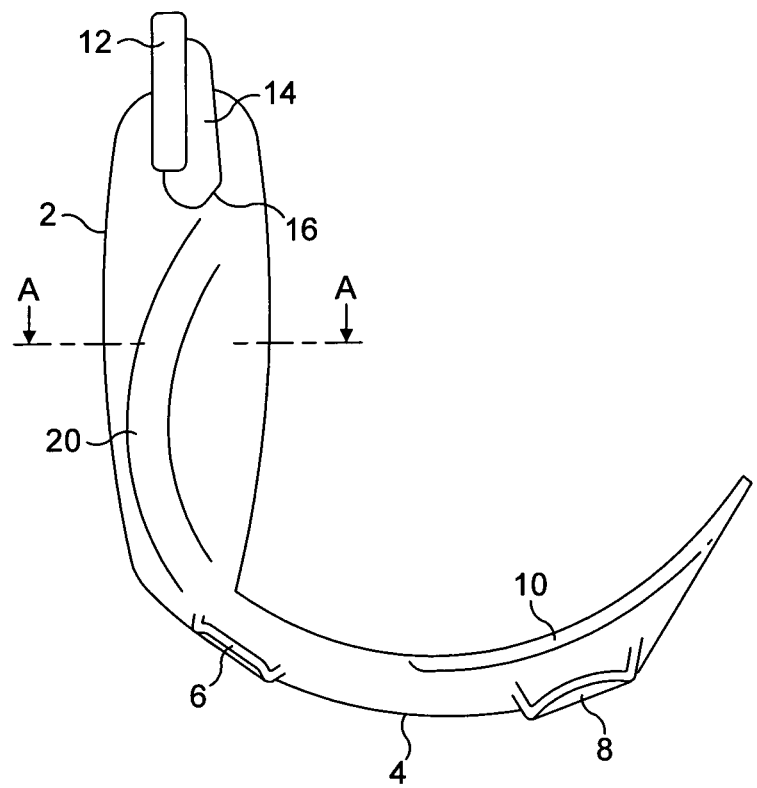
FIG. 3 is a lateral view of an alternative laryngoscope, without a retained tube.
Figure 4:
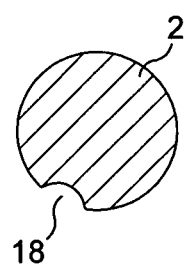
FIG. 4 is a cross-section through A-A'.
Figure 5:
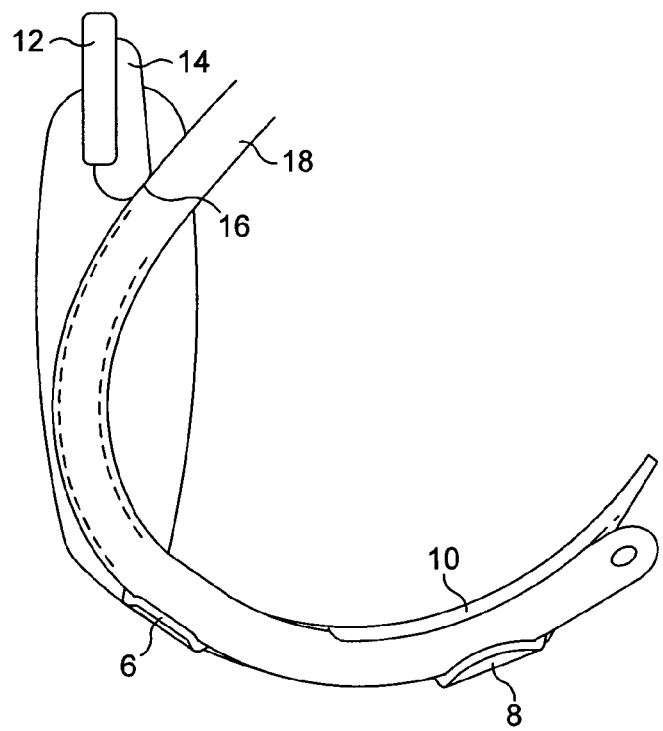
FIG. 5 is a lateral view of the laryngoscope of FIG. 3, with a retained tube.

FIGS. 3 through 5 illustrate an alternative laryngoscope further including a shallow groove 20 which functions as a tube guiding member, guiding a retained endotracheal tube. The groove is shallow such that a retained endotracheal tube predominantly extends from the surrounding handle surface. An intubator can hold the endotracheal tube against the handle with their grip. Because the tube is retained in flexural tension, no guiding member is required to resist lateral movement of the endotracheal tube relative to the handle. The endotracheal tube can easily be removed from contact with the video screen retaining protrusion by an intubator in use and advanced. Because the groove is shallow, the groove does not function to retain the endotracheal tube. As the tube is exposed, an intubator can readily grip the endotracheal tube with their spare hand. The handle is shaped such that an intubator can extend their grip around an endotracheal tube within the groove as well as at least the majority and perhaps all of the handle. The groove also functions to indicate where an endotracheal tube should be located when it is loaded and the path of curvature it should take.

Figure 6:
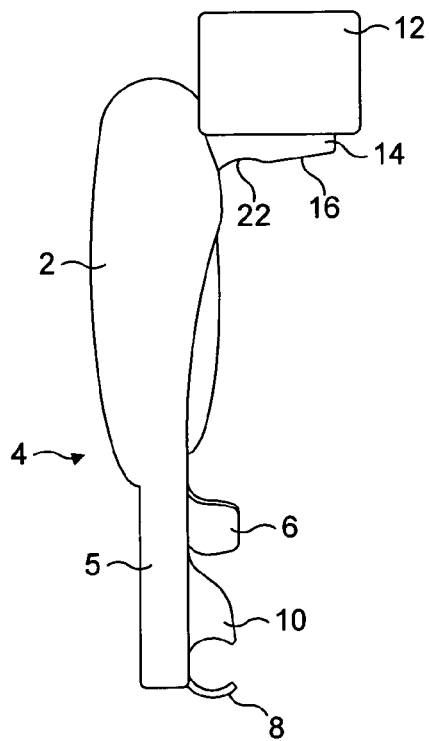
FIG. 6 is a side view of an alternative laryngoscope, without a retained tube.
Figure 7:
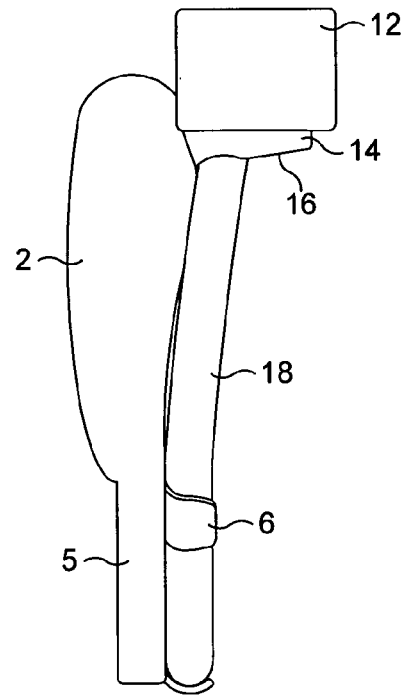
FIG. 7 is a side view of the laryngoscope of FIG. 6, with a retained tube.

In the embodiment illustrated in FIGS. 6 and 7, an endotracheal tube is retained along a path which is broadly along the length of the handle, with some lateral extent. The protruding video screen retaining arm (functioning as a protrusion) includes a shallow groove 22 so that the protrusion both retains and guides the endotracheal tube. As shown in FIGS. 6 and 7, the insertion section comprises an elongate member 5 within which the bore runs and from which the tube guiding members extend laterally.

Figure 8:
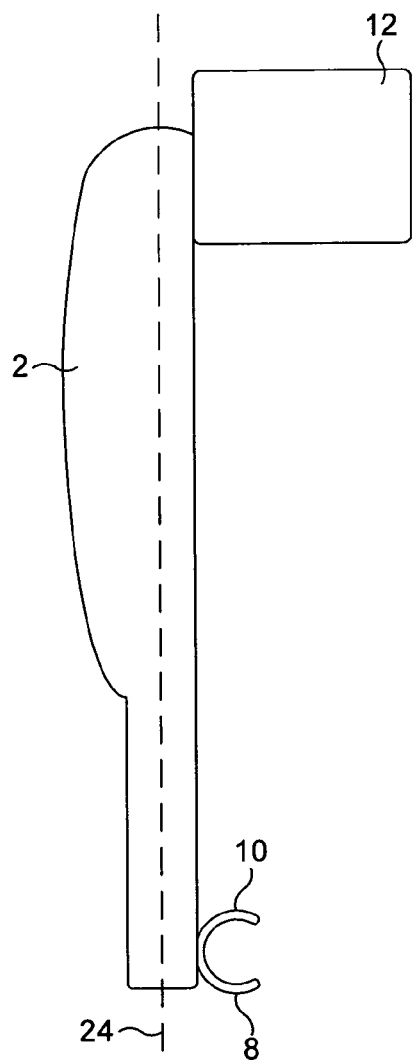
FIG. 8 is a side view of an alternative laryngoscope, without a retained tube.
Figure 9:
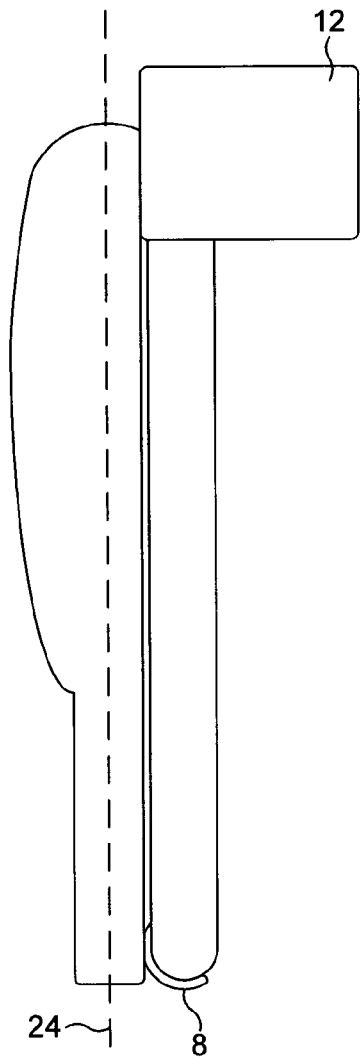
FIG. 9 is a side view of the laryngoscope of FIG. 8, with a retained tube.
Figure 10:
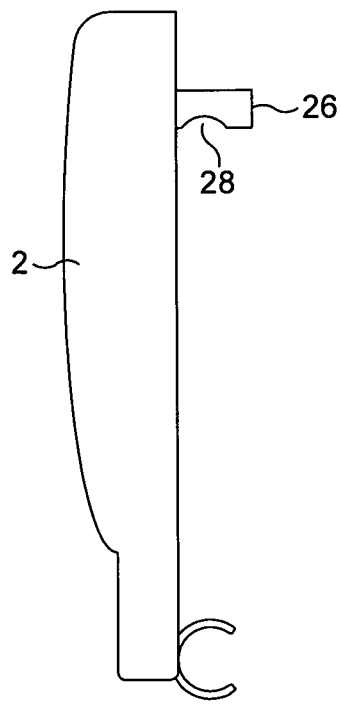
FIG. 10 is a side view of an alternative laryngoscope, without a retained tube.
Figure 11:
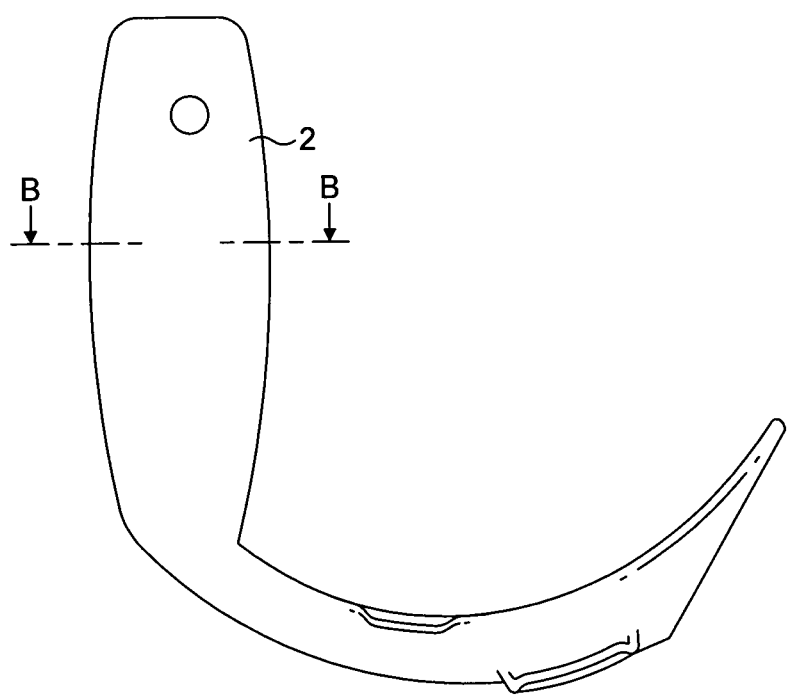
FIG. 11 is a lateral view of the laryngoscope of FIG. 10, without a retained tube.

In the embodiment illustrated in FIGS. 6 and 7, a retained endotracheal tube is not retained in a plane and is instead curved in a lateral direction. FIGS. 8 and 9 illustrate an alternative laryngoscope in which a retained endotracheal tube extends in a plane, parallel to the centre line 24 of the laryngoscope. This arrangement is advantageous in that lateral curvature in the retained endotracheal tube is avoided, reducing friction during insertion. Furthermore, the movement required to advance the endotracheal tube along its curved path is more natural and better resembles the motion required during intubation with conventional laryngoscopes.

FIGS. 10 to 12A illustrates an alternative laryngoscope which does not include a handle mounted video screen, comprising a protrusion 26 which extends laterally from near the distal end of the handle and includes a groove 28 on a distal side thereof for retaining and guiding an endotracheal tube. The handle has a smooth lateral side, on the same side of the laryngoscope as the protrusion and tube guide, enabling a tube to be retained on the laryngoscope parallel to the centre line of the laryngoscope, in a plane.

Figure 12A:
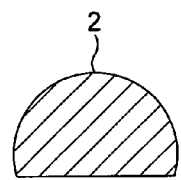
FIG. 12A is a cross-section through B-B in the laryngoscope of FIGS. 10 and 11.
Figure 12B:
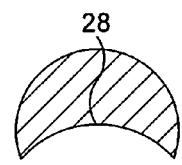
FIGS. 12B to 12L are cross-sections through alternative laryngoscope handles.
Figure 12C:
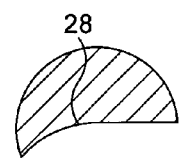
Figure 12D:
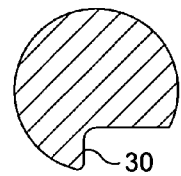
Figure 12E:
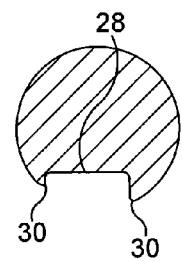
Figure 12F:
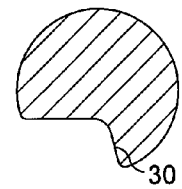
Figure 12G:
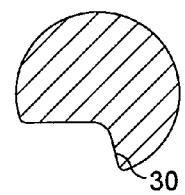
Figure 12H:
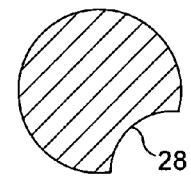
Figure 12I:
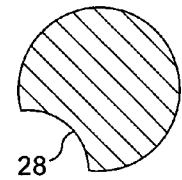
Figure 12J:
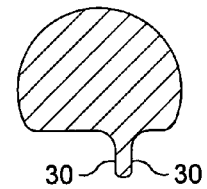
Figure 12K:
Figure 12L:
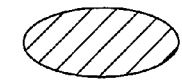

The handle may alternatively or additionally comprise a guide wall for guiding an endotracheal tube. FIGS. 12B through 12J illustrate cross-sections through alternative laryngoscope handles, including various combinations of grooves 28 and guide walls 30. In each of FIGS. 12B through 12J, an endotracheal tube with an external diameter at the lower end of an operating range of endotracheal tube diameters (5.5 mm in the case of an insertion section for use with an adult human) can be touched by a user whilst they grip the handle. FIGS. 12K and 12L illustrate handles without tube guides in at least one cross-section.

Figure 13:
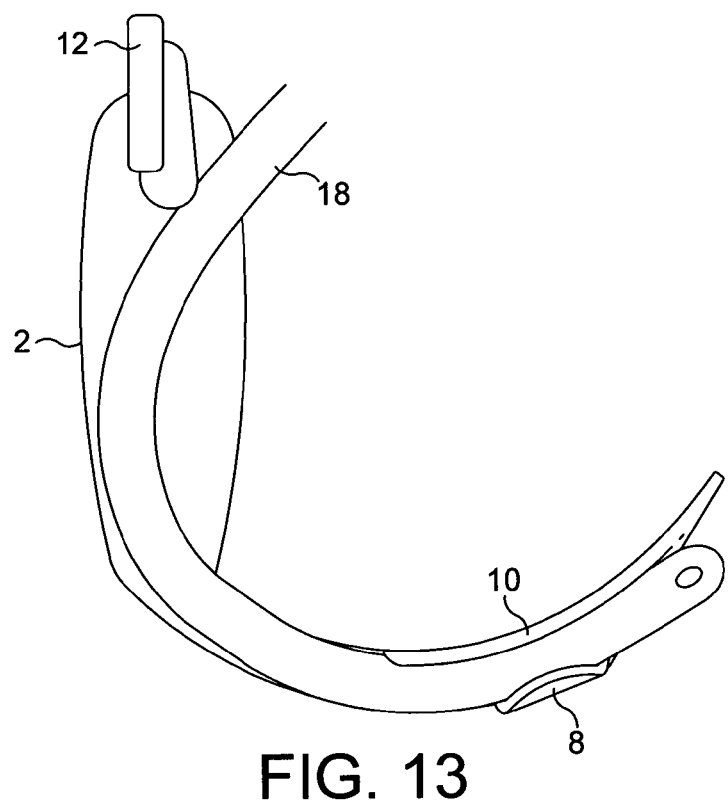
FIG. 13 is a side view of an alternative laryngoscope, with a retained large diameter tube.
Figure 14:
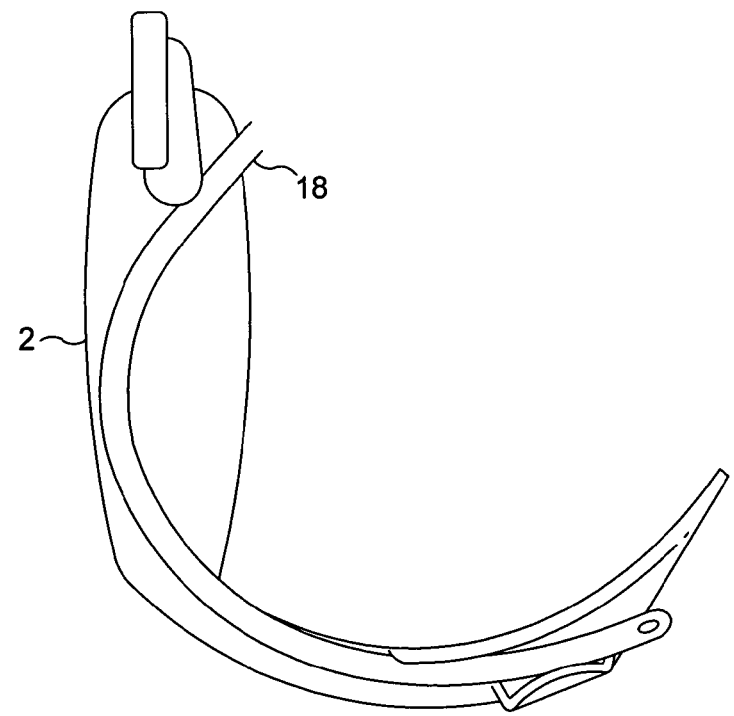
FIG. 14 is a side view of the laryngoscope of FIG. 13, with a retained small diameter tube.
Figure 15:
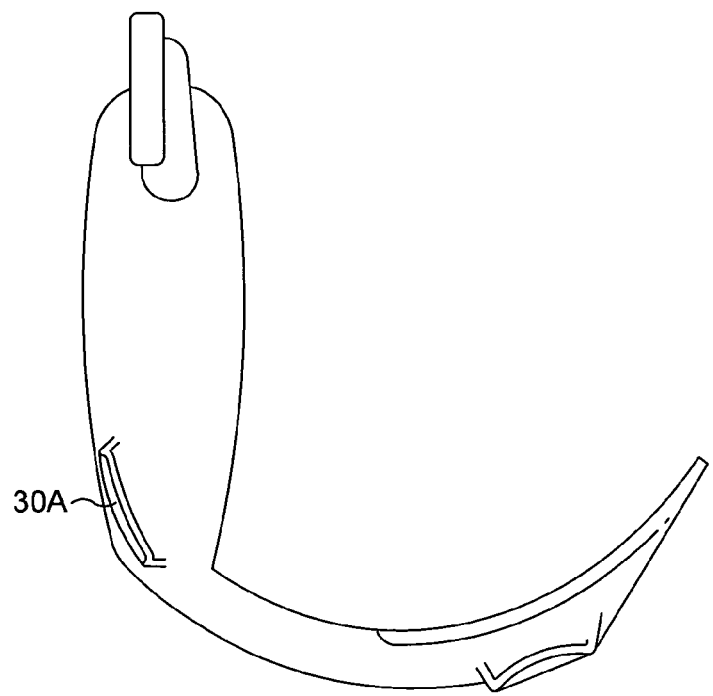
FIGS. 15 to 20 are side views of alternative laryngoscopes.
Figure 16:
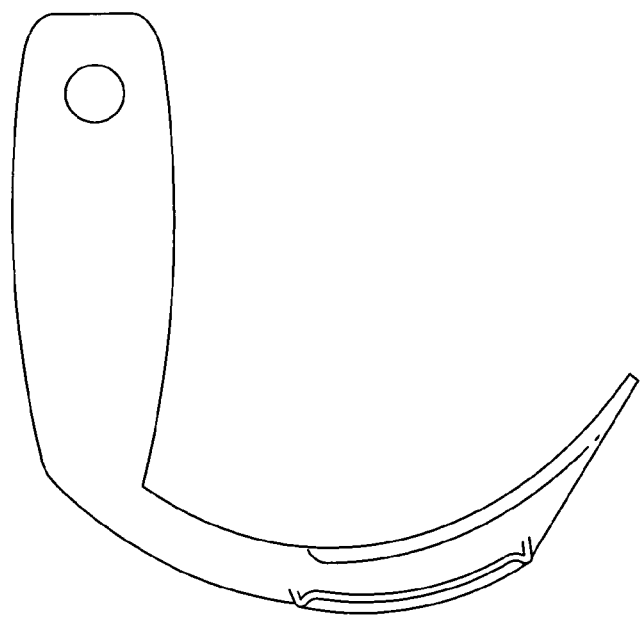
Figure 17:
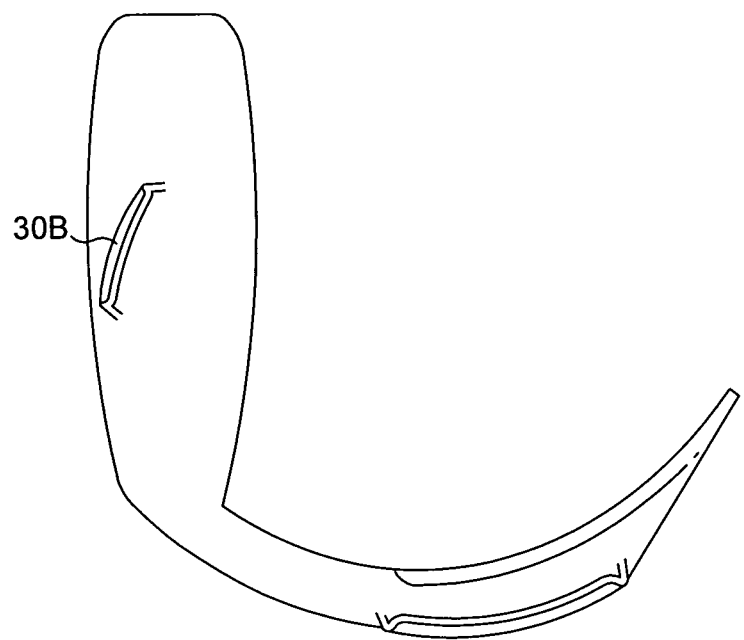
Figure 18:
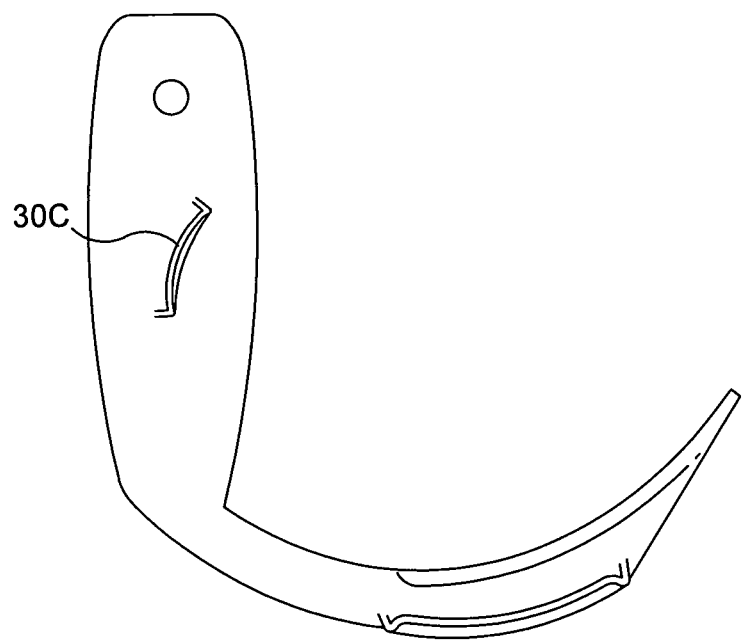
Figure 19:
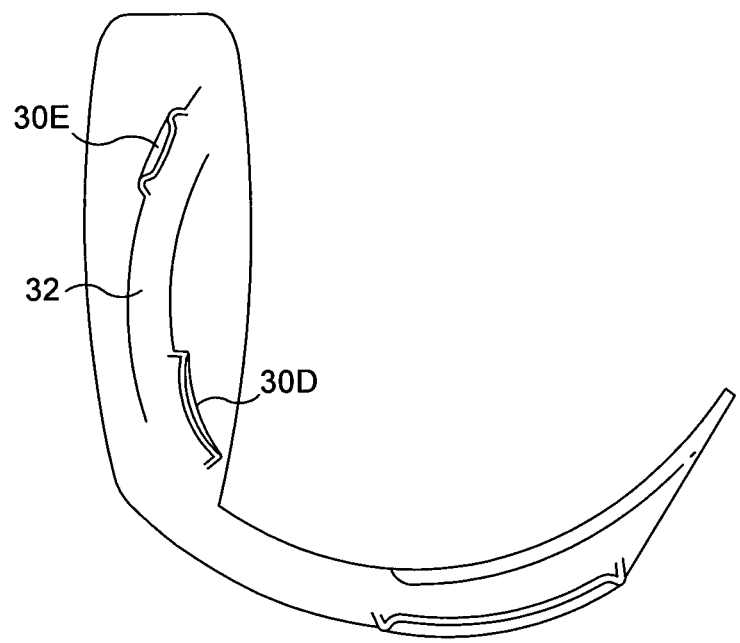
Figure 20:
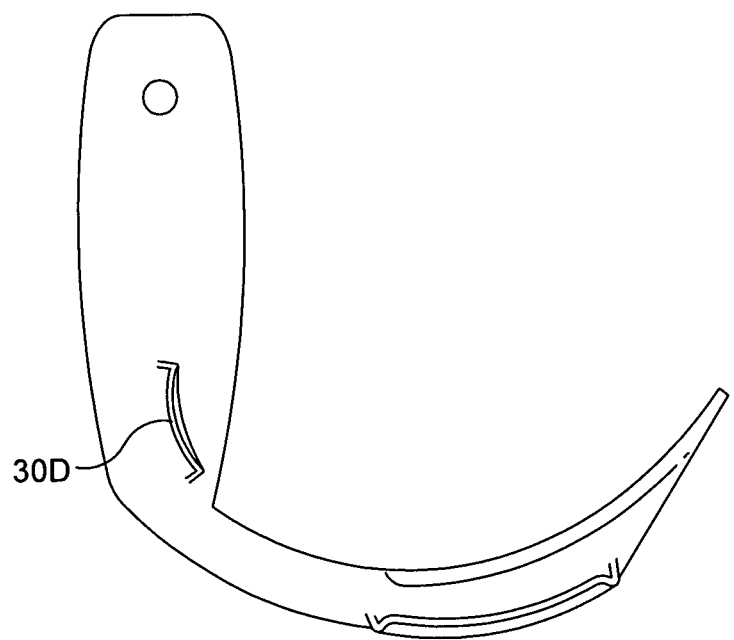

FIGS. 13 and 14 illustrate alternative laryngoscopes with tube retaining formations which can readily retain endotracheal tubes with different diameters. This embodiment does not include a proximal superior tube retaining member. As the retained tube extends from the surface of the handle, it can readily be grasped by an intubator and they can grip the handle and hold an endotracheal tube against the handle at once.

FIGS. 15 to 20 illustrate various alternative embodiments in which the laryngoscope includes at least one tube guiding member which extends laterally from the handle of the laryngoscope and functions to retain and guide an endotracheal tube. The tube guiding members may contact the superior side of a retained endotracheal tube (30A, 30B, 30E) or the inferior side (30D) and may contact a retained endotracheal tube in the distal half of the handle (30D), the proximal half of the handle (30C, 30E) or the middle of the handle (30B). An elongate groove 20 may be provided in combination with the tube guiding members.

In the examples described above and illustrated with reference to FIGS. 1 to 20, the laryngoscope comprises a body and removeable detachable disposable insertion section. Alternatively, the laryngoscope and insertion section may be permanently or semi-permanently joined. The laryngoscope with permanently or semi-permanently joined insertion section may be disposable.

Further modifications and variations may be made within the scope of the invention herein disclosed.

The invention claimed is:

1. A laryngoscope comprising:
   a handle and an insertion section which extends from the handle, the insertion section comprising a tube guide for retaining and guiding an endotracheal tube during intubation, wherein
   the handle comprises at least one external tube engaging formation with an overall length including a tube retaining member arranged to detachably retain on the handle the endotracheal tube which is received within the tube guide, such that at least a surface of the endotracheal tube is on an external surface of the handle,
   the at least one external tube engaging formation comprises a tube guiding member arranged to guide the endotracheal tube which is received within the tube guide along the handle,
   the at least one external tube engaging formation is arranged such that the endotracheal tube is contactable and pinchable by a user at a location within the overall length where the endotracheal tube is retained on and guided along the handle while a user grips the handle, and
   the laryngoscope is arranged to keep the endotracheal tube, while retained in the tube guide, continuously curved from a most proximal location where the laryngoscope contacts the endotracheal tube to a most distal location where the laryngoscope contacts a superior surface of the endotracheal tube.

2. A laryngoscope according to claim 1, wherein the tube guiding member comprises a groove on the external surface of the handle of the laryngoscope.

3. A laryngoscope according to claim 2, wherein the groove is configured so that the endotracheal tube remains at least partially exposed along at least a majority of the handle.

4. A laryngoscope according to claim 2, wherein the groove is configured so that either a most inferior or a most superior point on a surface of the endotracheal tube remains exposed along at least a majority of a length of the handle.

5. A laryngoscope according to claim 2, adapted for use in the intubation of human adults, wherein a depth of the groove is less than 6 mm at its deepest point.

6. A laryngoscope according to claim 1, wherein the tube guiding member comprises an elongate tube guiding wall.

7. A laryngoscope according to claim 1, wherein the handle is configured so that it can be grasped during intubation with an intubater's hand in contact with the endotracheal tube.

8. A laryngoscope according to claim 1, configured such that the endotracheal tube can be detached from the tube retaining member without the endotracheal tube being advanced or withdrawn within the tube guide.

9. A laryngoscope according to claim 1, configured such that the endotracheal tube can be detached from the tube retaining member without removing the endotracheal tube from the tube guide, such that the endotracheal tube is fully exposed proximally of a most proximal part of the insertion section which contacts the endotracheal tube.

10. A laryngoscope according to claim 1, wherein the tube retaining member comprises a tube retaining surface.

11. A laryngoscope according to claim 10, wherein the tube retaining surface is located on the handle at a location such that the endotracheal tube brought into tube retaining contact with at least one tube retaining surface is retained by virtue of flexural tension in the endotracheal tube.

12. A laryngoscope according to claim 11, wherein the tube retaining surface is located such that the endotracheal tube received within the tube guide of the insertion section has to be curved by more than its integral curvature to be brought into tube retaining contact with the tube retaining surface.

13. A laryngoscope according to claim 10, wherein the tube retaining surface is arranged to detachably retain the endotracheal tube without guiding the endotracheal tube.

14. A laryngoscope according to claim 10, wherein the tube retaining surface defines a tube guiding formation.

15. A laryngoscope according to claim 1, wherein the tube retaining member comprises at least one tube retaining protrusion which protrudes from the handle.

16. A laryngoscope according to claim 15, wherein the at least one tube retaining protrusion protrudes laterally from the handle.

17. A laryngoscope according to claim 15, wherein the at least one tube retaining protrusion comprises a video screen support for displaying images received from a video camera which is located within or attached to the insertion section.

18. A laryngoscope according to claim 1, wherein the tube retaining member is configured so that the endotracheal tube remains at least partially exposed along at least a majority of a length of the handle.

19. A laryngoscope according to claim 1, wherein the tube retaining member is configured so that either a most inferior or most superior point on the surface of the endotracheal tube remains exposed along at least a majority of a length of the handle.

20. A laryngoscope according to claim 1, wherein the tube retaining member is located within, or extends into, a proximal half of the handle.

21. A laryngoscope according to claim 1, wherein the tube guiding member protrudes from the handle to contact an inferior or superior surface of the endotracheal tube.

22. A laryngoscope according to claim 1, wherein the insertion section is continuously curved at least from the most proximal location where it contacts the endotracheal tube to the most distal location where it contacts a superior side of the endotracheal tube.

23. A laryngoscope according to claim 1, for use in the intubation of adults wherein a straight line distance from the most proximal location where the laryngoscope contacts the endotracheal tube to the most distal location where the laryngoscope contacts the superior side of the endotracheal tube is at least 200 mm.

24. A laryngoscope according to claim 1, arranged such that the endotracheal tube, of at least one external diameter within an operating range of external diameters, is curved by at least 90° between the most proximal location where the laryngoscope contacts the endotracheal tube and the most distal location where the laryngoscope contacts the superior side of the endotracheal tube.

25. A laryngoscope according to claim 1, arranged such that a path described by the endotracheal tube from the tube guide to a most proximal location where it contacts the handle is substantially within a plane.

26. A laryngoscope according to claim 25, arranged such that the path described by the endotracheal tube from the tube guide to the most proximal location where it contacts the handle is substantially parallel to a center line of the laryngoscope.

27. A laryngoscope according to claim 1, adapted to be used in a single intubation.

28. A laryngoscope according to claim 1, wherein the tube guide is arranged to hold a section of the endotracheal tube so that it extends along at least some of a length of the insertion section and the tube guide is a laterally opening tube guide from which the endotracheal tube may be removed in a substantially lateral direction.

29. A laryngoscope according to claim 28, wherein the insertion section comprises an elongate member having a lateral tube guide extending laterally therefrom and the at least one external tube retaining formation is provided on the same side of the laryngoscope as the lateral tube guide.

30. A laryngoscope according to claim 1, wherein the insertion section extends at an angle of at least 20° to a central axis of the handle.

31. A kit of parts comprising an insertion section and a laryngoscope body which comprises a handle, wherein the laryngoscope body and the insertion section comprise co-operating formations to enable the insertion section to be removeably attached to the body, wherein the insertion section comprises a tube guide for retaining and guiding an endotracheal tube during intubation and the handle comprises at least one tube engaging formation, the laryngoscope body and insertion section being arranged to form a laryngoscope according to claim 1 when the insertion section is removeably attached to the body.

32. A method of preparing a laryngoscope for an intubation procedure, comprising fitting an endotracheal tube to a tube guide of a laryngoscope according to claim 1, and engaging the tube guide with the at least one tube engaging formation of the laryngoscope body.

33. A laryngoscope according to claim 1, wherein the tube retaining member comprises a groove that is shallower than a diameter of the endotracheal tube such that where the endotracheal tube is retained on and guided along the handle the endotracheal tube is not recessed entirely within the groove.

34. A laryngoscope comprising:
- a handle and an insertion section which extends from a distal end of the handle, the handle and insertion section being adapted to detachably retain and guide an endotracheal tube along an external, lateral side surface of the insertion section and handle such that the endotracheal tube is continuously curved from a most proximal location where the handle contacts the endotracheal tube to a most distal location where the insertion section contacts a superior side of the endotracheal tube, wherein
- the handle comprises at least one external tube engaging formation with an overall length including a tube retaining member arranged to detachably retain on the handle an endotracheal tube which is received within a tube guide, such that at least a surface of a retained endotracheal tube is on the surface of the handle,
- the at least one external tube engaging formation comprises a tube guiding member arranged to guide the endotracheal tube which is received within the tube guide along the handle, and
- the at least one external tube engaging formation is arranged such that the endotracheal tube is contactable and pinchable by a user at a location within the overall length where the endotracheal tube is retained on and guided along the handle while a user grips the handle.

35. A laryngoscope according to claim 34, arranged such that, for endotracheal tubes with a range of external diameters within an operating range of endotracheal tube external diameters, the endotracheal tube is held in flexural tension from the most proximal location where the laryngoscope contacts a superior surface of the endotracheal tube to the most distal location where the laryngoscope contacts the superior surface of the endotracheal tube.

36. A laryngoscope according to claim 34, wherein the insertion section and handle each comprise external tube guiding members which detachably retain and guide the endotracheal tube along a lateral side surface of the insertion section and handle such that the endotracheal tube is continuously curved from the most proximal location where the handle contacts the endotracheal tube to the most distal location where the insertion section contacts the superior side of the endotracheal tube.

37. A laryngoscope according to claim 36, wherein the external tube guide members include at least two external tube guiding members, one of which is arranged to contact and guide the superior surface of the endotracheal tube and one of which is arranged to contact and guide an inferior surface of the endotracheal tube, and the handle comprises at least one of the at least two external tube guiding members.

38. A laryngoscope according to claim 36, wherein the tube guiding members are arranged to enable the endotracheal tube to be separated from the handle and insertion section within a patient without the laryngoscope being withdrawn.

39. A method of preparing a laryngoscope for an intubation procedure, comprising fitting an endotracheal tube to a tube guide of a laryngoscope according to claim 34.

40. A laryngoscope according to claim 34, wherein the tube retaining member comprises a groove that is shallower than a diameter of the endotracheal tube such that where the endotracheal tube is retained on and guided along the handle the endotracheal tube is not recessed entirely within the groove.

* * * * *